United States Patent [19]
Kimberly et al.

[11] Patent Number: 5,985,561
[45] Date of Patent: Nov. 16, 1999

[54] FC RECEPTOR POLYMORPHISM

[75] Inventors: Robert P. Kimberly; Jeffrey C. Edberg, both of Birmingham, Ala.

[73] Assignee: New York Society For The Relief Of The Ruptured and Crippled Maintaining The Hospital For Special Surgery, N.Y.

[21] Appl. No.: 08/868,279

[22] Filed: Jun. 3, 1997

Related U.S. Application Data

[60] Provisional application No. 60/019,129, Jun. 3, 1996.

[51] Int. Cl.$^6$ .............................. C12Q 1/68; C07H 21/02; C07H 21/04
[52] U.S. Cl. .............................. 435/6; 536/23.1; 536/24.3
[58] Field of Search ............................... 435/6; 536/23.1, 536/24.3; 935/76, 77, 78

[56] References Cited

U.S. PATENT DOCUMENTS 5,220,004  6/1993  Saiki et al. ............................ 536/24.31

OTHER PUBLICATIONS

D. Brian Dawson, *Clinical Biochemistry,* 23:279–285, 1990.
M. de Haas et al., *The Journal of Immunology,* 156:2948–2955, 1996.
J. Ravetech et al., *Journal of Experimental Medicine,* 170:481–497, 1989.
Vance et al., J. of Immunology 151(11): 6429–6439 (1993).
Radeke et al., J.of Immunology 153: 1281–1292 (1994).

*Primary Examiner*—W. Gary Jones
*Assistant Examiner*—Ethan Whisenant
*Attorney, Agent, or Firm*—Darby & Darby

[57] ABSTRACT

The present invention provides a method for identifying FcγRIIIA allelic pattern in a human patient. The present invention also provides methods for determining in a human patient a predisposition to autoimmune diseases and the relative capacity of a human subject to produce anti-tumor antibodies, antibodies directed against viral or bacterial pathogen, or to mount an effective immune response to a vaccine.

20 Claims, 1 Drawing Sheet

FIG. 1

FC RECEPTOR POLYMORPHISM

This application claims priority from U.S. Provisional Application Ser. No. 60/019,129, filed Jun. 3, 1996.

FIELD OF THE INVENTION

This invention pertains to a polymorphism in the human gene for FcγRIIIA that affects the function of the encoded receptor. The invention further pertains to methods for assessing the relative susceptibility of human patient populations to autoimmune diseases, bacterial and viral infections, and tumors, and to methods for gene therapy employing FcγRIIIA.

BACKGROUND OF THE INVENTION

Fc receptors are membrane glycoproteins present on the surface of neutrophils, macrophages and other cell types, whose primary function is to bind and internalize immunoglobulins, immune complexes, and immunoglobulinopsonized viruses, bacteria, and other particles. Three distinct families of human receptors for the Fc domain of immunoglobulin G (IgG) have been identified on the basis of reactivity with monoclonal antibodies, cellular distribution, and cDNA sequences: FcγRI, FcγRII, and FcγRIII. Within each of these three Fcγ receptor families, distinct genes and alternative splice variants lead to a series of receptor isoforms that have striking differences in their extracellular, transmembrane, and intracellular regions. The salient features of the known classes of Fcγ receptors are compiled in Table 1.

though the possible functional significance of these sequence variations is not yet clear. It is likely that more than two allelic forms exist for each Fcγ receptor gene.

The present inventors have identified a functionally significant allelic polymorphism in the FcγRIIIA gene, which results in the substitution of a valine for an phenylalanine at amino acid residue number 176 in the FcγRIIIA polypeptide (primary translation product). This amino acid substitution correlates with a differing ability of the two FcγRIIIA variants to bind IgG. Without wishing to be bound by theory, it is believed that the distribution of the FcγRIIIA isoform on monocytes, macrophages, mast cells, and, particularly, natural killer (NK) cells, as well as on kidney mesangial cells, means that this allelic polymorphism may affect the functioning of these cells in autoimmune diseases, tumor immunity, and antiviral and antibacterial immunity (and, in the case of mesangial cells, in mediating kidney disease). By contrast, an "expression polymorphism" was noted in one study that was interpreted as causing an apparent difference in the number (but not intrinsic binding capacity) of IgG binding sites on NK cells (Vance et al., *J.Immunol.* 151:6429, 1993).

Mononuclear phagocytes and NK cells lyse various target cell types via antibody-dependent cell-mediated cytotoxicity (ADCC). In ADCC, FcγRIIIA on the cytotoxic cell recognizes antibodies coating the surface of the target cells. Binding (and possibly aggregation) of FcγRIIIA then triggers synthesis and release of cytokines (such as, in the case of mononuclear phagocytes, interferon-γ, and in the case of NK cells, interleukin-2) as well as exocytic release of granules containing cytolytic compounds that effectuate

TABLE 1

| | Fcγ Receptor Families | | | | | | | |
|---|---|---|---|---|---|---|---|---|
| Structural Isoforms | FcγRI | | | FcγRII | | | Fcγ RIII | |
| Distinct genes | A | B | C | A | B | C | A | B |
| Splice variants | | + | (+) | a1, a2 | b1, b2, b3 | | | |
| Allelic variants | + | (+) | (+) | HR/LR | (+) | | | NA1<br>NA2 |
| Membrane anchor | TM | TM | (TM) | a1:TM<br>a2:secreted | TM | TM | γ/η/ζ<br>complex | GPI |
| Cell Distribution | | | | | | | | |
| Neutrophils | (+) | (?) | | + | | (?) | | + |
| Monocytes/Mφ | + | (?) | | + | (+)<br>~5% of<br>donors | (?) | + | |
| Lymphocytes | | | | | B cells | (?) | NK cells | |
| Mesangial cells of kidney | | | | | | | + | |

In addition to diversity based on distinct genes and their splice variants, different isoforms may also exhibit allelic polymorphisms. In several cases, the different alleles have been defined at the level of DNA sequence, and functional differences between the allelic forms have been noted. For example, the two recognized allelic forms of FcγRIIIB, NA1 and NA2, which differ by several amino acids and N-linked glycosylation sites, also differ in their capacity to mediate phagocytosis. In the case of FcγRIIA, the known allelic variants, HR ("high responder") and LR ("low responder"), which differ at amino acid position 131, differ substantially in their capacity to bind and internalize IgG2 (Salmon et al., 1992, *J. Clin. Invest.*, 89:1274). (In fact, FcγRIIA-LR is the only human FcγR that recognizes IgG2 efficiently.) Furthermore, allelic variants of FcγRI have also been found, lysis of the adjacent target cell. NK cells are also involved in lysis of some tumor cells and virally infected cells and participate in graft-versus-host disease (GVHD) reactions. Interestingly, occupancy of FcγRIIIA on the surface of NK cells, coupled with exposure of the cells to interleukin-2, has also been shown to induce apoptosis (programmed cell death) in NK cells (Ortaldo et al., *J. Exp.Med.* 181:339, 1995; Azzoni et al., *J. Immunol.* 154:491, 1995).

Because of the important role played by FcγRIIIA-bearing cells in many types of immune responses, there is a need in the art for diagnostic tests that predict the relative capabilities of FcγRIIIA-bearing cells in an individual to participate in FcγRIIIA-mediated reactions. Furthermore, there is a need for reagents and methods for gene therapy to supplement the FcγRIIIA polypeptides present on an individual's immune cells with alternate allelic forms of FcγRIIIA that are more effective in immune surveillance, immune complex clearing, and other processes.

SUMMARY OF THE INVENTION

The present invention encompasses methods for identifying the FcγRIIIA allelic pattern in a human patient, comprising obtaining genomic DNA from the patient and determining whether either or both copies of the FcγRIIIA gene contained therein comprises a pre-determined polymorphic DNA sequence. The determination may be achieved by: contacting the genomic DNA with an oligonucleotide specific for the pre-determined polymorphic DNA sequence, under conditions in which a hybrid can form between the oligonucleotide and its complement; and detecting any hybrid formed, wherein detection of a hybrid indicates the presence in at least one copy of the FcγRIIIA gene bearing the pre-determined polymorphic sequence. Alternatively, the determination may be achieved by purifying FcγRIIIA-expressing cells from a patient; extracting total RNA from the cells; and determining whether FcγRIIIA-encoding RNA comprises a pre-determined polymorphic sequence. In a preferred embodiment, the predetermined polymorphic sequence contains a G residue at position 559 of the FcγRIIIA gene. (The numbering is from residue 1 of FcγRIIIA cDNA, in which, for example, the initiator methionine is encoded by residues 34–36).

In another aspect, the invention encompasses methods for establishing statistically significant correlations between the presence in human populations of one or more polymorphisms in FcγRIIIA alleles and (i) the incidence and severity of particular autoimmune diseases; (ii) the incidence of malignancies and clinical outcome; (iii) the incidence and clinical manifestations of different bacterial and viral diseases, including AIDS; and (iv) the efficacy of different types of vaccines in inducing protective immunity against particular pathogens, tumor antigens, or other immunogens. Any clinical circumstance in which NK cells and/or antibody-dependent NK cell reactions are involved is within the scope of the invention. Similarly, physiologically significant reactions involving surface FcγRIIIA polypeptides on monocytes/macrophages, on mast cells, on brain glial cells, and on kidney mesangial cells are also within the scope of the invention.

In one embodiment, the present invention provides diagnostic methods for determining predisposition to severe forms of a particular autoimmune disease in a patient, such as, for example, autoimmune glomerulonephritis, comprising establishing a statistically significant correlation between an FcγRIIIA allelic pattern and severity of the particular autoimmune disease; identifying the FcγRIIIA allelic pattern encoded by the patient's DNA; comparing the patient's allelic pattern with the corresponding FcγRIIIA allelic patterns in patients suffering from mild forms of the disease, severe forms of the disease, and no disease; and determining which of the corresponding patterns is most similar to the patient's FcγRIIIA allelic pattern.

In another embodiment, the present invention provides a diagnostic method for determining relative capacity in a patient producing anti-tumor antibodies for mounting an effective FcγRIIIA-mediated tumor-killing response, comprising establishing a statistically significant correlation between an FcγRIIIA allelic pattern and incidence and clinical outcome of a particular malignancy; identifying the pattern of FcγRIIIA alleles encoded by the patient's DNA; comparing the pattern with the corresponding FcγRIIIA allelic patterns of humans with no malignancy, humans who experienced the particular malignancy and had a favorable clinical outcome, and humans who experienced the malignancy and had an unfavorable clinical outcome; and determining which of the corresponding patterns is most similar to the patient's FcγRIIIA allelic pattern.

In another embodiment, the invention provides a diagnostic method for determining the relative capacity in a patient producing antibodies directed against a viral or bacterial pathogen to mount an effective FcγRIIIA-mediated antibacterial or antiviral immune response, comprising establishing a statistically significant correlation between an FcγRIIIA allelic pattern and incidence and outcome of a particular bacterial or viral infection; identifying the pattern of FcγRIIIA alleles encoded by the patient's DNA; comparing the pattern with the corresponding FcγRIIIA allelic patterns of humans with no infection, humans who experienced the particular infection and had a favorable clinical outcome, and humans who experienced the particular infection and had an unfavorable clinical outcome; and determining which of the corresponding patterns is most similar to the patient's FcγRIIIA allelic pattern.

In another aspect, the invention provides methods for modifying the expression patterns of FcγRIIIA receptors in mononuclear phagocytes, NK cells, and/or kidney mesangial cells. These methods are carried out by using in vivo or ex vivo methods, or combinations thereof, to introduce nucleic acids encoding alternate alleles of FcγRIIIA receptors into the appropriate recipient cells.

DETAILED DESCRIPTION OF THE INVENTION

All patent applications, patents, and literature references cited in this specification are hereby incorporated by reference in their entirety. In the case of inconsistencies, the present description, including definitions, will control.

Definitions

1. "Allelic form" as used herein denotes an alternative version of a gene encoding the same functional protein but containing differences in its nucleotide sequence relative to another version of the same gene.

2. "Allelic polymorphism" or "allelic variant" as used herein denotes a variation in the nucleotide sequence within a gene, wherein different individuals in the general population may express different variants of the gene. A "predetermined polymorphic DNA sequence" is a known allelic variant.

3. "Allelic pattern" as used herein denotes the identity of each of the two copies of a particular gene in a patient, i.e., homozygosity for a particular allelic form, or heterozygosity encompassing two different allelic forms. The term "allelic pattern" is used interchangeably with "genotype".

4. "Amplification" of DNA as used herein denotes the use of polymerase chain reaction (PCR) to increase the concentration of a particular DNA sequence within a mixture of DNA sequences. For a description of PCR see Saiki et al., 1988, *Science,* 239:487.

5. "Chemical sequencing" of DNA denotes methods such as that of Maxam and Gilbert (Maxam-Gilbert sequencing, Maxam and Gilbert, 1977, *Proc. Natl. Acad. Sci. USA,* 74:560), in which DNA is randomly cleaved using individual base-specific reactions.

6. "Enzymatic sequencing" of DNA denotes methods such as that of Sanger (Sanger et al., 1977, *Proc. Natl. Acad. Sci. USA,* 74:5463), in which a single-stranded DNA is copied and randomly terminated using DNA polymerase.

7. "Severe" autoimmune disease as used herein is defined as autoimmune disease encompassing organ-threatening and/or life-threatening symptoms. Severe autoimmune disease is often associated with clinical manifestations such as nephritis, vasculitis, or lung disease, or combinations thereof, that require aggressive treatment and may be associated with premature death. "Mild" autoimmune disease encompasses symptoms that may be function-altering and/or comfort-altering, but are neither immediately organ-threatening nor life-threatening.

8. An "effective FcγRIIIA-mediated immune response" as used herein is an immune response that results in the lessening or amelioration of at least one symptom of the pathological condition or syndrome to which the immune response is directed. A "favorable" clinical outcome for a particular condition is defined as one in which the patient's condition improved; while an "unfavorable" clinical outcome is one in which the patient's condition worsened.

The present invention provides methods for determining the allelic pattern of FcγRIIIA genes in human patients. The methods encompass the use of allele-specific oligonucleotides as hybridization probes and/or as primers for DNA amplification, as well as the use of direct DNA sequencing. Identification of receptor alleles may also be achieved immunologically, by contacting blood cells that express FcγRIIIA receptors on their cell surface with antibodies that distinguish between different polymorphic forms of the receptor. In a preferred embodiment, the invention provides a method for identifying the T/G polymorphism at position 559 in the FcγRIIIA gene.

The present invention is based on the finding that an allelic polymorphism in the gene encoding the human FcγRIIIA receptor isoform results in functionally distinct gene products. The "conventional" version of the DNA encoding FcγRIIIA contains a T (thymine) at position 559; while the "polymorphic" version contains a G (guanine) at this position. (Nucleotide numbering is from position 1 in FcγRIIIA cDNA (Genbank Accession No. X52645 M31937). The substitution of G for T results in a change in the amino acid encoded at position 176 from phenylalanine to valine. (The amino acid numbering is in reference to the primary translation product, i.e., residue 1 corresponds to the initiator methionine.) As described in more detail in Example 3 below, the Phe→Val substitution correlates with a change in the capacity of the receptor to bind IgG. Consequently, it is believed that the expression of one or the other version of the receptor in an individual has important consequences for the physiological activity of the receptor and thus for the functioning of the cell types that carry the receptor, i.e., monocytes/macrophages, NK cells, mast cells, and mesangial cells in the kidney.

The present invention provides a method for identifying the FcγRIIIA allelic pattern in human patients, which comprises testing blood cells or DNA from individual patients for the presence of different FcγRIIIA allelic variants, using antibody-based and/or nucleic-acid-based methods which are described in more detail below. In a preferred embodiment, the method comprises determining whether each copy of the FcγRIIIA gene in the patient's DNA contains a T or a G residue at position 559 of the FcγRIIIA coding region and/or whether the FcγRIIIA polypeptides expressed at the surface of immune cells of the patient contain the corresponding phenylalanine or valine residue at position 176.

The present invention also encompasses the identification and analysis of new allelic forms of FcγRIIIA genes, which can be achieved using methods well-known in the art, such as, for example, DNA sequencing (with or without prior amplification of FcγRIIIA DNA segments); single-strand conformational polymorphism analysis (SSCP) (Ravnik-Glavac et al., *Hum. Mol. Genet.,* 3:801, 1994); "HOT" cleavage (Cotton, et al., *Proc. Natl. Acad. Sci., USA,* 85:4397, 1988); denaturing gradient gel electrophoresis (DDGE) (Guldberg et al., *Nuc. Acids Res.,* 22:880, 1994); and combinations of the foregoing. Once a new polymorphism has been identified, immunological and/or molecular biological tests can be used to screen patients for the presence or absence of the polymorphism, as described for the T/G polymorphism at position 559. For example, monoclonal antibodies specific to the protein encoded by the newly identified allele can be prepared by well-known methods; these antibodies can then be used for screening of patient populations as described above. Alternatively, allele-specific oligonucleotides can be designed for use as probes and/or as primers in hybridization or PCR-based detection methods, respectively.

The invention also encompasses the establishment of statistically significant correlations, where they exist, between different allelic forms of FcγRIIIA (and allelic patterns formed by combinations of different alleles) and various physiological and/or clinical manifestations of variable FcγRIIIA function. For example, since FcγRIIIA is expressed on NK cells, monocyte/macrophages, mast cells, and mesangial cells in the kidney, polymorphisms that affect IgG binding by the receptor may affect any of the functions of these cells that are dependent on, and/or are initiated by, interaction of the receptor with antibody. Such functions include lysis of viruses and/or virally-infected cells; bacterial ingestion and killing; tumor cell killing; and reactions important in autoimmune diseases, such as, for example, clearing of immune complexes. Consequently, in practicing the present invention, correlations are sought between particular FcγRIIIA allelic forms and, for example: the risk of glomerulonephritis (mesangial cells and mononuclear phagocytes); the effectiveness of antibodies protective against viral infection or against tumor neo-antigens (NK cells); and the risk of immune complex disease (mononuclear phagocytes).

Accordingly, studies are performed in which the incidence of disease caused by different viral and bacterial infections, as well as the clinical course and outcome, is correlated with particular FcγRIIIA allelic patterns. Similarly, the incidence of different types of malignancies (and clinical course and outcome) is correlated with particular FcγRIIIA allelic patterns. Finally, qualitative or quantitative aspects of particular autoimmune diseases, e.g., the number, severity, and duration of symptoms; the need for medication or other ameliorative treatment; and other clinical parameters, are also correlated with particular FcγRIIIA allelic patterns.

To establish these correlations, where they exist, the distribution of FcγRIIIA allelic patterns in a large number (several hundred) patients suffering from (or having a history of) viral or bacterial infection, malignancies, or autoimmune disease is determined using any of the methods described below, and compared with the distribution of FcγRIIIA allelic patterns in control (i.e., healthy) patients that have been matched for age and ethnic origin. A statistical method such as a 2×3 Chi square test is then used to determine whether the allele frequencies in the disease and normal groups are the same or different. In this manner, it is possible to obtain statistically significant correlations between a given pathological syndrome and FcγRIIIA alleles. It is believed that correlations between particular FcγRIIIA genotypes and particular diseases will provide an important prognosticator of disease susceptibility and clinical outcome.

Once a statistically significant correlation has been established between a clinically significant variable or symptom or susceptibility and a particular FcγRIIIA allelic pattern, screening tests are devised to detect the particular allelic patterns in appropriate patient populations.

Determination of Fcγ receptor genotypes according to the present invention may be performed in a susceptible population; alternatively, such testing can be performed after an initial diagnosis has been made. In this manner, different therapeutic interventions may be chosen for optimal long-term benefit. It will be understood that the particular FcγRIIIA allele that is screened for, the starting patient populations that are the targets of screening, and the test populations that provide the appropriate statistical database, will vary with the particular disease or syndrome. In one case, if a given FcγRIIIA allele is rare, but is found to be strongly associated with a particular syndrome, large-scale screening may be appropriate if early therapeutic intervention can reduce or ameliorate later development of symptoms. For example, if a patient is found to express an FcγRIIIA allele that is associated with increased risk of particular complications, the patient might be treated prophylactically before the complications develop. Alternatively, a given FcγRIIIA allele may be common in the general population, and thus not be suitable for random screening. The same allele, however, when found in a patient already known to be suffering from a particular disease or syndrome, may correlate with the subsequent development of more severe manifestations of the disease. In this case, identification of a patient's FcγRIIIA genotype according to the present invention is performed after an initial diagnosis of the disease.

In practicing the present invention, the FcγRIIIA allelic pattern in an individual patient is determined by either: 1) immunological detection of one or more allelic forms of FcγRIIIA polypeptides present on the surface of appropriate immune cells ("phenotypic characterization"); or 2) molecular detection of the DNA or RNA encoding one or more FcγRIIIA allelic forms using nucleic acid probes, with or without nucleic acid amplification or sequencing ("genotypic characterization").

In the first method, white blood cells or subsets thereof are isolated from a patient to be tested using methods that are well known in the art, such as, for example, gradient centrifugation and/or immunoadsorption. Antibodies that are capable of distinguishing between different allelic forms of FcγRIIIA are then applied to the isolated cells to determine the presence and relative amount of each allelic form. The antibodies may be polyclonal or monoclonal, preferably monoclonal. Measurement of specific antibody binding to cells may be accomplished by any known method, including without limitation quantitative flow cytometry, or enzyme-linked or fluorescence-linked immunoassay. The presence or absence of a particular allele, as well as the allelic pattern (i.e. homozygosity vs. heterozygosity) is determined by comparing the values obtained from the patient with norms established from populations of patients of known gentoypes.

In an alternate embodiment, DNA is obtained from a patient, and the presence of DNA sequences corresponding to particular Fcγ receptor alleles is determined. The DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, and tissue exudates at the site of infection or inflammation. DNA is extracted from the cell source or body fluid using any of the numerous methods that are standard in the art. It will be understood that the particular method used to extract DNA will depend on the nature of the source.

Once extracted, the DNA may be employed in the present invention without further manipulation. Alternatively, the DNA region corresponding to all or part of the FcγRIIIA may be amplified by PCR or other amplification methods known in the art. In this case, the amplified regions are specified by the choice of particular flanking sequences for use as primers. Amplification at this step provides the advantage of increasing the concentration of FcγRIIIA DNA sequences. The length of DNA sequence that can be amplified ranges from 80 bp to up to 30 kbp. Preferably, primers are used that define a relatively short segment containing sequences that differ between different allelic forms of the receptor.

The presence of Fcγ receptor allele-specific DNA sequences may be determined by any known method, including without limitation direct DNA sequencing, hybridization with allele-specific oligonucleotides, and single-stranded conformational polymorphism (SSCP). Direct sequencing may be accomplished by chemical sequencing, using the Maxam-Gilbert method, or by enzymatic sequencing, using the Sanger method. In the latter case, specific oligonucleotides are synthesized using standard methods and used as primers for the dideoxynucleotide sequencing reaction.

Preferably, DNA from a patient is subjected to amplification by polymerase chain reaction (PCR) using specific amplification primers, followed by hybridization with allele-specific oligonucleotides. Alternatively, SSCP analysis of the amplified DNA regions may be used to determine the allelic pattern. Most preferably, allele-specific PCR is used, in which allele-specific oligonucleotides are used as primers and the presence or absence of an amplification product indicates the presence or absence of a particular allele.

In an alternate embodiment, cells expressing FcγRIIIA are isolated by immunoadsorption, and RNA is isolated from the immunopurified cells using well-known methods such as guanidium thiocyanate-phenol-chloroform extraction (Chomocyznski et al., 1987, *Anal. Biochem.*, 162:156.) The isolated RNA is then subjected to coupled reverse transcription and amplification by polymerase chain reaction (RT-PCR), using allele-specific oligonucleotide primers. Conditions for primer annealing are chosen to ensure specific reverse transcription and amplification; thus, the appearance of an amplification product is diagnostic of the presence of the allele specified by the particular primer employed. In another embodiment, RNA encoding FcγRIIIA is reverse-transcribed and amplified in an allele-independent manner, after which the amplified Fcγ receptor-encoding cDNA is identified by hybridization to allele-specific oligonucleotides or by direct DNA sequencing.

Functional Implications of FcγRIIIA Allelic Polymorphism

As described in more detail in Example 3 below, the two allelic forms of FcγRIIIA that differ only in the presence of Phe or Val at position 176 differ markedly in their ability to bind IgG. IgG binding to FcγRIIIA is typically quantified by contacting FcγRIIIA-expressing cells with IgG that has been labelled. The labelled moiety may be labelled, for example, by fluorescence or radioactivity. Alternatively, the primary IgG may be unlabelled, and a secondary, labelled antibody or other moiety may be used to detect bound primary IgG. The only condition is that the labelling procedure and/or presence of the label does not interfere with the receptor-ligand interaction. Following incubation, unbound IgG is removed by washing, and the amount of IgG bound to the cells is measured by any appropriate means. As shown in Example 3, FcγRIIIA receptor polypeptides containing Val at position 176 bind IgG more efficiently than wild-type (i.e., $Phe_{176}$-containing) receptors.

In one embodiment, binding of IgG to FcγRIIIA polypeptides is measured using purified cell populations that consist of, e.g., purified NK cells, purified macrophages, and the like. In general, methods for cell purification are well-known in the art and may comprise without limitation: flow cytometry; density gradient centrifugation to obtain mononuclear cells; depletion of mononuclear phagocytes by adhesion to an appropriate solid support; negative selection (i.e., depletion) of different cell types by reaction with cell-type-specific monoclonal antibodies; and combinations of the foregoing. Alternatively, multicolor flow cytometry can be used to identify a particular desired cell type (such as, e.g., NK cells) and to analyze IgG binding to that cell type, even without physical purification of the cells. The possible finding that an FcγRIIIA polymorphism selectively affects the functioning of particular FcγRIIIA-bearing cell types would allow the design of appropriate cell type-specific therapeutic regimens.

In another embodiment, binding of IgG to FcγRIIIA polypeptides is measured using purified IgG subclasses, i.e., purified IgG1, IgG2, IgG3, and IgG4. The possible finding that a particular FcγRIIIA polymorphism affects receptor binding to a subset of IgG subclasses would be important in circumstances in which specific antigens elicit antibodies that are restricted to particular subclasses.

The present invention also encompasses the identification of other functional consequences of the Phe→Val substitution or of other allelic variations in the FcγRIIIA sequence. In one embodiment, cells expressing different allelic forms of FcγRIIIA are tested for their ability to mediate antibody-dependent cell-mediated cytotoxicity (ADCC), using chicken erythrocytes (CE) coated with rabbit anti-CE IgG as target cells (see Example 4 below).

In another embodiment, the ability of different allelic forms of FcγRIIIA to support apoptosis of FcγRIIIA-expressing interleukin 2 (IL-2)-activated NK cells is quantified. In this assay, NK cells are first activated with IL-2 and then exposed to an IgG ligand capable of cross-linking cell-surface FcγRIIIA polypeptides. Cell death is then determined by methods well-known in the art, such as, for example, by visually monitoring trypan blue exclusion or by quantifying propidium iodide uptake by flow cytometry in combination with monoclonal antibodies directed against NK cell-surface components.

It will be understood that different allelic forms of FcγRIIIA may differentially affect the ability of NK cells to engage different effector mechanisms, such as, for example, lytic or homeostatic reactions (the former exemplified by tumor cell killing and the latter by regulation of NK cell populations). Similarly, different allelic forms of FcγRIIIA may differentially affect the ability of monocytes and macrophages to, e.g., clear immune complexes or trigger immune reactions. Furthermore, different allelic forms of FcγRIIIA may affect receptor-mediated intracellular signalling events such as $[Ca^{+2}]i$ fluxes, and/or receptor-mediated increases in expression of HLA Class II molecules and interleukin-2 receptor molecules.

Applications

The present invention finds use in diagnostic and therapeutic methods that are based upon the existence of genetic polymorphisms in the FcγRIIIA gene that result in functional differences in the gene products.

Diagnostics

Cancer: FcγRIIIA-bearing cells such as NK cells and macrophages are thought to play an important role in immunological surveillance against developing malignancies. Accordingly, it is believed that, for certain types of maligancies at least, the statistical analyses described above will reveal statistically significant correlations between FcγRIIIA allelic patterns and at least one identifiable clinical parameter of cancer, such as, for example, survival time, response to chemotherapy or radiation therapy, extent of metastasis, and the like. If such correlations exist, appropriate screening tests for FcγRIIIA allelic patterns could be utilized to tailor therapeutic programs for each patient. These screening tests may be particularly applicable to patients in which treatment strategies are designed to evoke anti-tumor antibodies. Any tumor to which there is a host immune response involving antibodies that bind FcγRIIIA is within the scope of the invention. A non-limiting example of a malignancy to which the methods of the present invention can be applied is malignant melanoma.

Viral and bacterial infections: Different FcγRIIIA-bearing immune cells are thought to play important roles in combatting infection, macrophages play a primary role against bacterial infection and NK cells against viral infection. Any statistically significant correlation that is found to exist between FcγRIIIA allelic patterns and any clinical parameters of viral or bacterial infection, such as, e.g., susceptibility to infection, recurrence of infection, responsivity to antibiotics or antiviral agents, duration of infection, and the like, would enable the use of appropriate screening tests for FcγRIIIA allelic patterns as part of a diagnostic battery. Any infectious disease that evokes an immune response involving antibodies that bind FcγRIIIA is within the scope of the invention. Non-limiting examples include bacterial diseases such as those caused by Streptococcus, Staphylococcus, Pneumococcus, and Hemophilus influenzae, and viral diseases such as those caused by influenza virus, adenoviruses, and human immunodeficiency virus.

Autoimmune diseases: The autoimmune diseases to which the methods of the present invention can be applied include without limitation systemic lupus erythematosus (SLE); systemic vasculitides such as Wegener's granulomatosis, polyarteritis nodosa, and cryoglobulinemic vasculitis; Sjogren's syndrome; mixed connective tissue disease; rheumatoid arthritis; and kidney diseases such as glomerulonephritis. The clinical manifestations of these diseases range from mild to severe. Mild autoimmune disease encompasses symptoms that may be function-altering and/or comfort-altering, but are neither immediately organ-threatening nor life-threatening. Severe autoimmune disease encompasses autoimmune disease encompassing organ-threatening and/or life-threatening symptoms. Severe autoimmune disease is often associated with clinical manifestations such as nephritis, vasculitis, or lung disease, or combinations thereof, that require aggressive treatment and may be associated with premature death. Any statistically significant correlation that is found to exist between FcγRIIIA allelic patterns and any clinical parameters of autoimmune disease would enable the use of appropriate screening tests for FcγRIIIA allelic patterns as part of a diagnostic battery.

Vaccine efficacy: Individuals vary greatly in their response to different vaccines. In addition to differences in the level of antibodies elicited in different patients in response to a particular vaccine, the varying level of protection against the infectious agent may be due at least in part to a difference in the ability of FcγRIIIA-bearing immune cells to bind and/or lyse the infectious agent. Without wishing to be bound by theory, it is contemplated that even pre-existing test vaccines thought not to be effective (or to be only marginally effective) may in fact be effective only in individuals carrying certain FcγRIIIA allelic patterns. It is also contemplated that patients whose FcγRIIIA polypeptides bind IgG less effectively may benefit from higher than conventional doses of immunogen (leading to higher threshold antibody levels) in order to achieve protective immunity. Accordingly, it is believed that in designing vaccine trials, stratifying patients by FcγRIIIA genotype would provide important information regarding vaccine efficacy.

Biologics: Therapeutic agents are currently being designed in which portions of the IgG Fc region are coupled to therapeutic moieties in order to prolong the in vivo half-life of the agents. For example, the monoclonal antibody OKT3 (Orthoclone), which is used clinically as an immunosuppressant, causes a variety of side effects (including Cytokine Release Syndrome). At least some of these side effects are likely to involve interaction of the administered antibody with FcγRIIIA receptors. (An example of Fcγ receptor-mediated side effects of an exogenously administered monoclonal antibody in a mouse system is described in Alegre et al., *J.Immunol.* 155:1544, 1995.) It is contemplated that the susceptibility of different patients to at least some of the side-effects of these agents may be correlated to their FcγRIIIA allelic patterns. Accordingly, pre-treatment screening of candidate patients using the methods of the present invention would provide an important benefit in achieving the most effective use of these agents.

Soluble forms of FcγRIIIA have also been reported to be cytotoxic for certain myeloma cells (Hoover et al., *J. Clin. Invest.* 95:241, 1995). It is contemplated that the differing ability of different allelic forms of FcγRIIIA to bind IgG according to the present invention will be an important influence on efficacy of the different allelic forms in adjunctive immunotherapy.

Therapeutics

The differential ability of different allelic forms of FcγRIIIA to bind IgG, and the corresponding differential response of patients bearing different FcγRIIIA allelic patterns to particular physiological stimuli means that it may be desirable to alter the FcγRIIIA expression patterns in patients for therapeutic purposes. This may be achieved by modifying FcγRIIIA expression levels (such as, for example, in mononuclear phagocytes by cytokine treatment with transforming growth factor-γ or interferon-α) and/or by modifying the allelic forms of FcγRIIIA expressed in particular cells using gene transfer techniques. The phagocytic activity of macrophages, for example, makes them particularly suitable as recipients of FcγRIIIA-encoding nucleic acids.

The FcγRIIIA-encoding nucleic acids may be DNA or RNA, and include sense and antisense sequences. The nucleic acids may be flanked by their native regulatory sequences, or may be associated with heterologous sequences, including promoters, enhancers, response elements, signal sequences, polyadenylation sequences, introns, 5'- and 3'- noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also included. The nucleic acid may be derivatized by formation of a methyl or ethyl phosphotriester or an alkyl phosphoramidate linkage. Preferably, the sequences are present in appropriate nucleic acid vectors operably linked to regulatory sequences that allow their expression in the recipient cells. The expression may be transient or long-term, depending upon the expression system that is utilized. Any appropriate means for delivering the FcγRIIIA-encoding nucleic acids to the recipient cells may be used, including packaging in liposomes or recombinant viruses. Furthermore, both in vivo and ex vivo approaches may be used. For in vivo approaches, the nucleic acids are introduced directly into the patient; for ex vivo approaches, appropriate recipient cells are first removed from the patient and contacted with the FcγRIIIA-encoding nucleic acids under conditions appropriate for uptake and expression, after which the transformed cells are re-introduced into the patient.

FcγRIIIA-encoding nucleic acids may also be introduced into cells by recombination events, for example, by homologous recombination at the site of the endogenous gene or a sequence with substantial identity to the gene. Other recombination-based methods such as nonhomologous recombinations or deletion of endogenous genes by homologous recombination may also be used.

It will be understood that the particular vectors and delivery systems used in practicing the present invention may vary, depending upon the particular recipient cell type, the purpose for which treatment is performed, and other variables. For example, the amount of a particular vector, virus, or liposome preparation to be administered can be determined by experimentation known in the art, such as by establishing a matrix of dosages and frequencies and comparing a group of experimental units or subjects to each point in the matrix. Similarly, the therapeutic effects of a particular formulation are also determined by methods known in the art for each pathological condition or syndrome being treated. Any lessening or amelioration of any clinical signs or symptoms of a particular condition or syndrome that is achieved by administration of nucleic acids encoding an allelic variant of FcγRIIIA is within the scope of the invention.

The following working examples are intended to serve as non-limiting illustrations of the present invention.

EXAMPLE 1

Determination of FcγRIIIA Allelic Patterns by DNA Amplification and Sequencing The following studies were performed to identify allelic polymorphisms in the FcγRIII gene sequences.

Cell and RNA Isolation: Fresh anticoagulated human peripheral blood was separated by centrifugation through a discontinuous two-step Ficoll-Hypaque gradient (Salmon et al., 1990, *J. Clin. Invest.*, 85:1287). Polymorphonuclear leukocytes (PMNs) were isolated from the lower interface and washed with HBSS (Gibco Laboratories, Grand Island, N.Y.). Contaminating erythrocytes were lysed with hypotonic saline (0.02% NaCl) for 20 seconds followed by 0.16% NaCl and a final wash with HBSS. Mononuclear cells were isolated from the upper interface and washed with HBSS. RNA was then isolated from the mononuclear cell fraction using a phenol-guanidine thiocyanate-based procedure (TRIzol Reagent, Life Technologies, Gaithersburg Md.).

RT-PCR Amplification of the FcγRIIIA coding sequence: Two sets of oligonucleotide primers were chosen to generate overlapping amplification products that together encompass the entire FcγRIIIA coding region. These primers are shown below. (In each case, the sequence shown in bold is the sense or antisense sequence corresponding to an FcγRIIIA sequence, while the underlined sequence is an M13 sequence).

Set 1: sense primer

5'-CAGGAAACAGCTATGACCTCCCAACTGCTCTGCTACTT-3' antisense primer

5'-TGTAAAACGACGGCCAGTCCTCAGGT-GAATAGGGTCTTC-3'

Set 2: sense primer

5'-TGTAAAACGACGGCCAGTCCGGTGCAGCTAGAAGTCCA-3' antisense primer

5'-CAGGAAACAGCTATGACCGGGGTTG-CAAATCCAGAGAA-3'

Typically, 1–5 ng of RNA is incorporated into a 20 μl reaction containing 0.5 μg oligo(dT), 1 μl of a mix containing 10 mM of each deoxyribonucleotide triphosphate and 200 U reverse transcriptase in an RT-PCR reaction buffer (SuperScript Preamplification System, Gibco BRL). The reverse transcription reaction is carried out for 50 min at 42° C. The reaction is terminated and the RNA template is removed by addition of 2 U RNase H and incubation at 37° C. for 20 min. Then, the reaction is supplemented with 2 U of Taq DNA polymerase and deoxyribonucleotides to a final concentration of 200 nM. The following cycles of amplification are performed in a DNA Thermal Cycler (Perkin-Elmer Cetus, Norwalk, Conn.): Three cycles are performed consisting of 94° C., 3 min; 57° C., 45 sec; and 72° C., 1.5 min. Thirty cycles of amplification are then performed consisting of 94° C., 1 min; 59° C., 45 sec; and 72° C., 1.5 min. Finally, the amplification products are extended at 72° C. for 10 min, after which the reaction is chilled at 4° C. The resulting amplified products are then analyzed by electrophoresis in 1.5% agarose gels, followed by staining with ethidium bromide, according to standard procedures.

DNA Sequencing: The PCR product described above is isolated from agarose gels using GeneClean II (Bio 101, La Jolla, Calif.), and subjected to automated cycle sequencing using ABI PRISM™ M13 dye primer kits and AmpliTaq™ DNA polymerase (Perkin-Elmer). DNA sequences are routinely determined from both strands, using sense or antisense primers, and reactions are analyzed on an ABI PRISM™ 377 automated sequencer (ABI/Perkin-Elmer).

RESULTS

The following sequencing results were obtained from 29 individuals. The sequences were identical, except at position 559. At this position, 9 individuals were T/T homozygotes, 17 were T/G heterozygotes, and 3 were G/G homozygotes. All of these individuals had FcγRIIIA genes containing a T residue at position 230 (de Haas et al., *J. Immunol.* 156:2948, 1996).

EXAMPLE 2

Determination of FcγRIIIA Allelic Patterns Without Prior Cell Separation

The following approach is used to determine the FcγRIIIA allelic pattern in a patient, without the necessity for purifying mononuclear cells prior to analysis. This is achieved by using amplification primers that are specific for the FcγRIIIA gene. DNA is isolated from a patient from any available cell source.

(a) Nucleotides 486–640 of the FcγRIIIA gene are amplified using the following primers. (In each case, the sequence shown in bold is the sense or antisense sequence corresponding to an FcγRIIIA sequence, while the underlined sequence is an M13 sequence).

sense primer, SEQ ID NO: 1

5'-CAGGAAACAGCTATGACCTCATCATAATTCTGACTTCC-3' antisense primer, SEQ ID NO: 2

5'-TGTAAAACGACGGCCAGTCTTGAGT-GATGGTGATGTTCA-3'

DNA is amplified and subjected to cycle sequencing as described in Example 1 above.

(b) In an alternative approach, allele-specific amplification is performed using (i) a sense primer that corresponds precisely to an FcγRIIIA-specific sequence upstream of nucleotide 559 (as shown, nucleotides 486–505) and (ii) antisense primers that correspond either to the "T" allele or the "G" allele of FcγRIIIA at nucleotide 559. The rationale is that the pattern of amplification is indicative of the presence of either T or G at position 559. Representative primers are shown below:

sense primer, SEQ ID NO: 3

5'-TCATCATAATTCTGACTTCC-3' antisense primers:

5'-AAGACACATTTTTACTCCCAAA-3' ("T" allele-specific, SEQ ID NO:4)

5'-AAGACACATTTTTACTCCCAAC-3' ("G" allele-specific, SEQ ID NO: 5)

The primers are designed with intentional mismatches, if necessary, to optimize the allele-specific hybridization (and thus, allele-specific amplification) within a single reaction.

EXAMPLE 3

IgG Binding to Different FcγRIIIA Allelic Forms

The following studies were performed to compare the ability of immune cells carrying different allelic forms of FcγRIIIA receptors to bind IgG.

Anticoagulated peripheral blood was obtained from each individual, and the cells were washed with phosphate-buffered saline (PBS) to remove the plasma. The cells were incubated with 30 μg/ml FITC-labelled polyclonal human IgG (Sigma Chemical Co.) for 30 min at 4° C., after which the unbound antibody was removed and the cells washed in PBS.

Bound IgG was quantified by flow cytometry using a FACScan (Becton Dickinson Immunocytometry Systems, Mountain View, Calif.). For each experiment, the instrument was calibrated with standardized fluorescence microbead standards (Flow Cytometry Standards Corp., Research Triangle Park, N.C.) to allow assessment of both absolute and relative levels of immunofluorescence.

Figure 1:
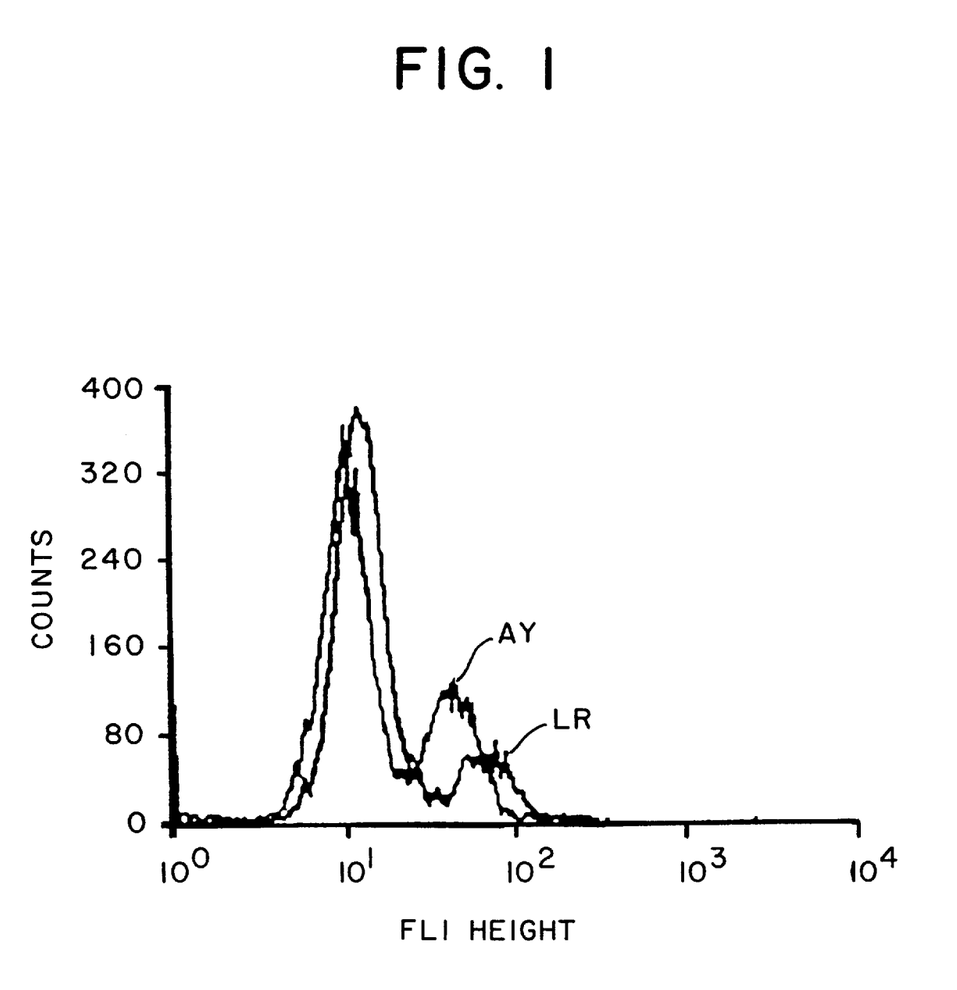
FIG. 1 is a graphic representation of the results of a flow cytometry experiment which compared the binding of IgG to blood cells from two different patients. The X axis represents the fluorescence intensity exhibited by each cell, and the Y axis represents the number of cells in the sample that exhibited a particular fluorescence intensity. Independently, patient "AY" was shown to be homozygous for the version of the FcγRIIIA gene that contains a T residue at position 559, while patient "LR" was shown to be homozygous for an alternate allelic version of the gene that contains a G residue at position 559.

The results of a typical comparison between flow cytometry patterns obtained from patients with different FcγRIIIA allelic patterns is shown in FIG. 1. Cells obtained from Patient "LR", a G/G homozygote at position 559 of the FcγRIIIA gene, bind significantly more IgG on a per cell basis than those obtained from patient "AY", a "T/T" homozygote at position 559 of the FcγRIIIA gene.

Table 2 shows the results of a study in which matched donor pairs from patients having different FcγRIIIA allelic patterns at position 559 were compared with respect to IgG binding. In A, the samples were incubated with fluorescently-labelled IgG1; in B, the samples were incubated with unlabelled IgG1, followed by fluorescently-labelled anti-IgG; and in C, the samples were incubated with fluorescently-labelled pooled IgG. In parallel, each sample was incubated with a monoclonal antibody (mAb) that recognizes FcγRIIIA irrespective of the amino acid sequence at residue 176. The numbers represent the position of the fluorescence peak on the X axis of a histogram such as that shown in FIG. 1. (Each horizontal row in Table 2 represents a single experiment using matched donor pairs with constant settings and antibody concentrations; the numbers vary from experiment to experiment due to instrument settings).

TABLE 2

| Genotype | G/G | | T/T | |
|---|---|---|---|---|
| Fluorescence | IgG | mAb | IgG | mAb |
| A) IgG1 direct | 61 | 1672 | 13 | 1663 |
| | 65 | 1673 | 11 | 2008 |
| | 16 | 59 | 11 | 48 |
| B) IgG1 indirect | 106 | 269 | 40 | 304 |
| C) pooled IgG | 67 | 101 | 43 | 97 |
| | 60 | 61 | 28 | 64 |
| | 60 | 61 | 39 | 102 |

The results indicate that FcγRIIIA receptors containing valine at position 176 (i.e., encoded by DNA having a G at nucleotide 559) bind significantly more IgG on a molecule-by-molecule basis than do FcγRIIIA receptors containing phenylalanine at position 176 (i.e., encoded by DNA having a T at nucleotide 559).

EXAMPLE 4

Measurement of Antibody-Dependent Cell-Mediated Cytotoxicity (ADCC)

The following studies are performed to compare the ability of immune cells carrying different allelic forms of FcγRIIIA receptors to mediate ADCC. The methods are essentially those described in Vance et al., *J.Immunol.* 151:6429, 1993.

NK cells (effector cells) isolated as described in Example 1 above are resuspended in Medium 199 (M199) supplemented with 10% fetal bovine serum to give different effector:target ratios. To obtain fresh chicken erythrocyte (CE) target cells, wing vein blood is obtained on the day of the experiment, and the cells are washed three times in M199. 50 μl of packed CE are then incubated in an additional 50 μl of M199 and 50 μl of $^{51}$Cr (sodium chromate, DuPont-NEN, Boston Mass.) at 2 mCi/ml for 1 h at 37° C., after which the cells are washed twice with 10 ml M199 and resuspended at a concentration of $2.5 \times 10^5$ cells/ml.

50 μl each of effector and labelled target cells and 50 μl of anti-CE IgG are added to wells of a 96-well roundbottom plate and incubated for increasing times at 37° C. in a humidified atmosphere containing 5% $CO_2$. 85 μl aliquots of the supernatants are harvested and transferred to 2-mm glass tubes and counted in a gamma counter.

The percentage of cytotoxicity is calculated as 100 x (counts release with effectors+antibody)−(counts release with effectors alone)/(maximum lysis-spontaneous release). Maximum lysis is estimated by adding 50 μl of labelled target cells to 100 μl of a 20% SDS solution and harvesting 85 μl of the supernatant. The nonspecific cytotoxicity is estimated by adding 50 μl of labelled target cells to 100 μl M199 and harvesting 85 μl of the supernatant.

RESULTS: It is anticipated that cells bearing FcγRIIIA allelic forms that bind IgG relatively less efficiently will also be less effective at ADCC.

We claim:

1. A method for identifying the FcγRIIIA allelic pattern in a human patient, said method comprising:
   (i) obtaining genomic DNA from said patient, and
   (ii) determining whether either or both copies of the FcγRIIIA gene contained in said genomic DNA comprises a pre-determined polymorphic DNA sequence.

2. A method as defined in claim 1, wherein the determining step comprises:
   (a) contacting said genomic DNA with an oligonucleotide specific for said pre-determined polymorphic DNA sequence, under conditions in which a hybrid can form between said oligonucleotide and and its complement; and
   (b) detecting any hybrid formed in step (a),
   wherein detection of said hybrid indicates the presence in at least one copy of the FcγRIIIA gene of said pre-determined polymorphic sequence.

3. A method as defined in claim 2, further comprising amplifying a region of the FcγRIIIA genes contained in said genomic DNA spanning said pre-determined polymorphic sequence prior to said contacting step.

4. A method as defined in claim 1, wherein said polymorphic sequence contains a G residue at position 559 of the FcγRIIIA gene.

5. A method for identifying the FcγRIIIA allelic pattern in a human patient, said method comprising:

(i) purifying FcγR-expressing cells from said patient;
   (ii) extracting total RNA from said cells;
   (iii) determining whether FcγRIIIA-encoding RNA contained in said total RNA comprises a pre-determined polymorphic RNA sequence.

6. A method as defined in claim 5, wherein said determining step comprises subjecting said RNA to coupled reverse transcription-polymerase chain reaction, under conditions in which RNA containing said pre-determined polymorphic sequence is selectively transcribed and/or amplified.

7. A method as defined in claim 6, wherein said determining step further comprises sequencing the products of said coupled reverse transcription-polymerase chain reaction.

8. A method as defined in claim 5, wherein said polymorphic sequence contains a G residue at position 559 of the FcγRIIIA gene.

9. A diagnostic method for determining predisposition to severe forms of an autoimmune disease in a patient, comprising
   (i) establishing a statistically significant correlation between an FcγRIIIA allelic pattern and severity of said autoimmune disease;
   (ii) identifying the corresponding FcγRIIIA allelic pattern of said patient;
   (iii) comparing the FcγRIIIA allelic pattern of said patient with the corresponding allelic patterns of humans with no autoimmune disease, mild forms of said autoimmune disease, and severe forms of said autoimmune disease; and (iv) determining which of said corresponding allelic patterns is most similar to the allelic pattern of said patient, wherein if the FcγRIIIA allelic pattern of said patient is most similar to the corresponding allelic pattern of human with severe forms of said autoimmune disease, said patient has a predisposition to severe forms of said autoimmune disease.

10. A diagnostic method as defined in claim 9, wherein said identifying comprises
   (a) obtaining genomic DNA from said patient, and
   (b) determining whether either or both copies of the FcγRIIIA gene contained in said genomic DNA comprises a pre-determined polymorphic DNA sequence.

11. A diagnostic method as defined in claim 9, wherein said identifying comprises
   (a) purifying FcγR-expressing cells from said patient;
   (b) extracting total RNA from said cells;
   (c) determining whether FcγRIIIA-encoding RNA contained in said total RNA comprises a pre-determined polymorphic RNA sequence.

12. A diagnostic method for determining relative capacity in a patient producing anti-tumor antibodies for mounting an effective FcγRIIIA-mediated tumor-killing response, comprising
   (i) establishing a statistically significant correlation between an FcγRIIIA allelic pattern and incidence and clinical outcome of a particular malignancy;
   (ii) identifying the corresponding FcγRIIIA allelic pattern of said patient;
   (iii) comparing the FcγRIIIA allelic pattern of said patient with the corresponding allelic patterns of humans with no malignancy, humans who experienced the particular malignancy and had a favorable clinical outcome; and humans who experienced the particular malignancy and had an unfavorable clinical outcome; and
   (iv) determining which of said corresponding allelic patterns is most similar to the allelic pattern of said patient.

13. A diagnostic method as defined in claim 12, wherein said identifying comprises
   (a) obtaining genomic DNA from said patient, and
   (b) determining whether either or both copies of the FcγRIIIA gene contained in said genomic DNA comprises a pre-determined polymorphic DNA sequence.

14. A diagnostic method as defined in claim 12, wherein said identifying comprises
   (a) purifying FcγR-expressing cells from said patient;
   (b) extracting total RNA from said cells;
   (c) determining whether FcγRIIIA-encoding RNA contained in said total RNA comprises a pre-determined polymorphic RNA sequence.

15. A diagnostic method for determining relative capacity in a patient producing antibodies directed against a viral or bacterial pathogen to mount an effective FcγRIIIA-mediated antibacterial or antiviral immune response, comprising (i) establishing a statistically significant correlation between an FcγRIIIA allelic pattern and incidence and clinical outcome of a particular bacterial or viral infection;
(ii) identifying the corresponding FcγRIIIA allelic pattern of said patient;
(iii) comparing the FcγRIIIA allelic pattern of said patient with the corresponding allelic patterns of humans with no infection, humans who experienced the particular infection and had a favorable clinical outcome; and humans who experienced the particular infection and had an unfavorable clinical outcome; and
(iv) determining which of said corresponding allelic patterns is most similar to the allelic pattern of said patient.

16. A diagnostic method as defined in claim 15, wherein said identifying comprises
   (a) obtaining genomic DNA from said patient, and
   (b) determining whether either or both copies of the FcγRIIIA gene contained in said genomic DNA comprises a pre-determined polymorphic DNA sequence.

17. A diagnostic method as defined in claim 15, wherein said identifying comprises
   (a) purifying FcγR-expressing cells from said patient;
   (b) extracting total RNA from said cells;
   (c) determining whether FcγRIIIA-encoding RNA contained in said total RNA comprises a pre-determined polymorphic RNA sequence.

18. A diagnostic method for determining relative capacity in a patient to mount an effective immune response to a vaccine, wherein said immune response is mediated at least in part by FcγRIIIA, said method comprising
   (i) establishing a statistically significant correlation between an FcγRIIIA allelic pattern and the efficacy of the immune response to said vaccine;
   (ii) identifying the corresponding FcγRIIIA allelic pattern of said patient;
   (iii) comparing the FcγRIIIA allelic pattern of said patient with the corresponding allelic patterns of humans exhibiting an optimal immune response to said vaccine and humans exhibiting a sub-optimal immune response to said vaccine; and
   (iv) determining which of said corresponding allelic patterns is most similar to the allelic pattern of said patient.

19. A diagnostic method as defined in claim 18, wherein said identifying comprises
   (a) obtaining genomic DNA from said patient, and
   (b) determining whether either or both copies of the FcγRIIIA gene contained in said genomic DNA comprises a predetermined polymorphic DNA sequence.

20. A diagnostic method as defined in claim 18, wherein said identifying comprises
   (a) purifying FcγR-expressing cells from said patient;
   (b) extracting total RNA from said cells;
   (c) determining whether FcγRIIIA-encoding RNA contained in said total RNA comprises a pre-determined polymorphic RNA sequence.

* * * * *

SEQUENCE LISTING

<160> NUMBER OF SEQ ID NOS: 5

<210> SEQ ID NO 1
<211> LENGTH: 38
<212> TYPE: DNA
<213> ORGANISM: Artificial Sequence
<220> FEATURE:
<223> OTHER INFORMATION: Primer with M13 and Human FcRIIIA Receptor
      Sequence

<400> SEQUENCE: 1

-continued

```
caggaaacag ctatgacctc atcataattc tgacttcc                    38

<210> SEQ ID NO 2
<211> LENGTH: 39
<212> TYPE: DNA
<213> ORGANISM: Artificial Sequence
<220> FEATURE:
<223> OTHER INFORMATION: Primer with M13 and Human FcRIIIA Receptor
      Sequence

<400> SEQUENCE: 2
tgtaaaacga cggccagtct tgagtgatgg tgatgttca                   39

<210> SEQ ID NO 3
<211> LENGTH: 20
<212> TYPE: DNA
<213> ORGANISM: Human FcRIIIA Receptor

<400> SEQUENCE: 3
tcatcataat tctgacttcc                                        20

<210> SEQ ID NO 4
<211> LENGTH: 22
<212> TYPE: DNA
<213> ORGANISM: Human FcRIIIA Receptor

<400> SEQUENCE: 4
aagacacatt tttactccca aa                                     22

<210> SEQ ID NO 5
<211> LENGTH: 22
<212> TYPE: DNA
<213> ORGANISM: Human FcRIIIA Receptor

<400> SEQUENCE: 5
aagacacatt tttactccca ac                                     22
```